United States Patent [19]

Rosenberg

[11] Patent Number: 4,645,490

[45] Date of Patent: Feb. 24, 1987

[54] NEPHROSTOMY CATHETER WITH FORMED TIP

[75] Inventor: Helmut W. G. Rosenberg, McHenry, Ill.

[73] Assignee: The Kendall Company, Boston, Mass.

[21] Appl. No.: 683,056

[22] Filed: Dec. 18, 1984

[51] Int. Cl.⁴ ............................................. A61M 29/00
[52] U.S. Cl. .................................................... 604/103
[58] Field of Search ................................. 604/99–103, 604/282, 284, 244, 905; 128/325, 656, 658, 348.1, 394; 524/436

[56] References Cited

U.S. PATENT DOCUMENTS

| | | | |
|---|---|---|---|
| 3,169,529 | 2/1965 | Koenig | 128/345 |
| 3,605,750 | 9/1921 | Sheridan | 128/658 |
| 3,634,924 | 1/1972 | Blake | 604/103 |
| 3,884,242 | 5/1975 | Bazelle | 604/103 |
| 3,978,863 | 9/1976 | Fettel et al. | 128/348.1 |
| 4,148,319 | 4/1979 | Kasper et al. | 604/170 |
| 4,405,314 | 9/1983 | Cope | 604/99 |
| 4,545,390 | 10/1985 | Leary | 128/344 |

OTHER PUBLICATIONS

*A.C.M.I. Catheters & Accessories,* 1960, p. 15.

*Primary Examiner*—John D. Yasko
*Attorney, Agent, or Firm*—Powell L. Sprunger

[57] ABSTRACT

A nephrostomy catheter comprising, an elongated shaft having a drainage lumen extending along the shaft and a distal end, and a formed tip bonded to the distal end of the shaft and having a distal opening communicating with the lumen to receive a guide wire.

1 Claim, 7 Drawing Figures

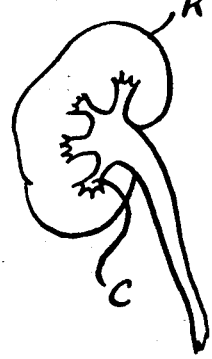
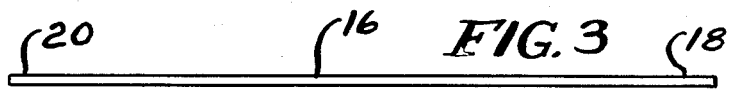
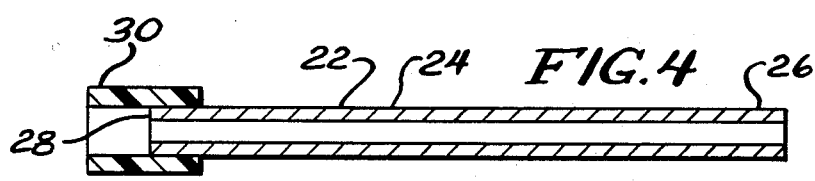
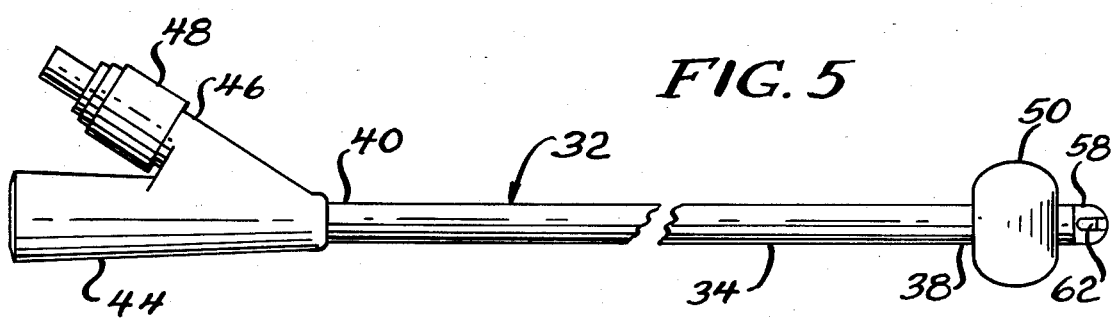
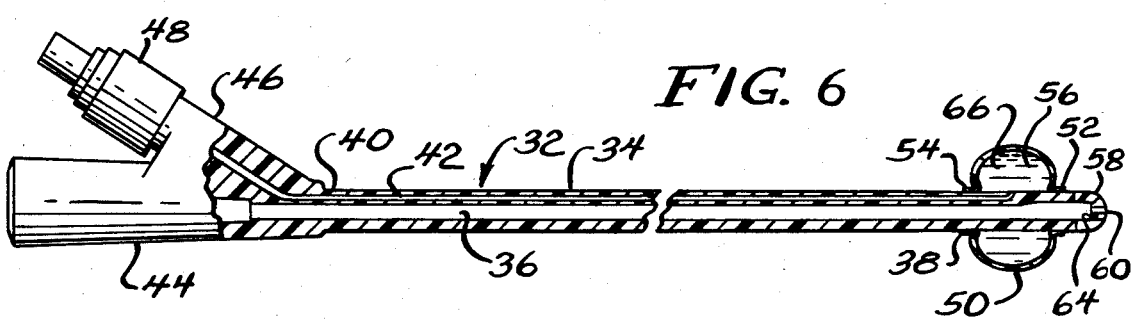
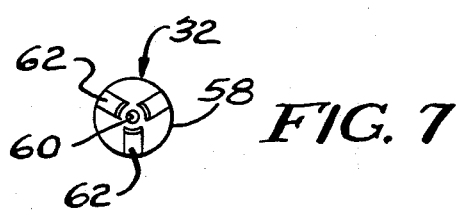

NEPHROSTOMY CATHETER WITH FORMED TIP

BACKGROUND OF THE INVENTION

The present invention relates to catheters.

When the ureter or kidney of a patient is obstructed by a stone, it is necessary to stabilize the kidney through drainage because an increase of pressure in the kidney could result in loss of the kidney. Such a procedure is called a nephrostomy procedure. First, a small gauge hollow needle is passed under radiologic vision until a tip of the needle is located in the renal calyces to obtain access to the kidney chamber. With the needle in place, a flexible elongated guide wire is passed through the needle, and the needle is removed with the guide wire in place to establish a path to the kidney. Next, a plurality of dilators are inserted over the guide wire in order to increase the size of the path to the kidney, and the dilators are then removed. In the past, a catheter is then placed over the guide wire, with the catheter having a pig tail which is located in the kidney. Although nephrostomy has been completed in this manner, it is desired to improve the procedure.

SUMMARY OF THE INVENTION

A principal feature of the present invention is the provision of an improved catheter for performing a nephrostomy procedure.

The catheter of the present invention comprises, an elongated shaft having a drainage lumen extending along the shaft and a distal end, and a formed tip bonded to a distal end of the shaft.

A feature of the present invention is that the tip has a distal opening communicating with the lumen to receive a guide wire.

Another feature of the invention is that the tip has at least one drainage eye intermediate the opening and a proximal end of the tip in order to drain urine from a kidney.

Yet another feature of the invention is that the tip defines an inner flat shoulder to receive a distal end of a stylet.

Another feature of the invention is that the elastic sleeve may be bonded to a distal portion of the shaft with a radiopaque adhesive.

A further feature of the invention is the provision of methods for performing a nephrostomy procedure.

Another feature of the present invention is the provision of a stylet having a proximal hollow flexible tube to prevent kinking of a guide wire.

Further features will become more fully apparent in the following description of the embodiments of this invention and from the appended claims.

DESCRIPTION OF THE DRAWINGS

In the drawings:

FIG. 1 is a diagrammatic view of a kidney of a patient;

FIG. 2 is an elevational view of a needle for performing a nephrostomy procedure;

FIG. 3 is an elevational view of a guide wire for performing the procedure;

FIG. 4 is an elevational view of a stylet for performing the procedure;

FIG. 5 is a fragmentary elevational view of a catheter of the present invention;

FIG. 6 is a fragmentary sectional view of the catheter of FIG. 5; and

FIG. 7 is an end view of a tip of the catheter of FIGS. 5 and 6.

DESCRIPTION OF THE PREFERRED EMBODIMENTS

Referring now to FIG. 1, there is shown a kidney K of a patient having a hollow renal calyces C. Referring to FIG. 2, there is shown a hollow needle 10 having a distal sharp tip 12 and a proximal hub 14. Referring to FIG. 3, there is shown an elongated guide wire 16 of flexible material having a distal end 18 and a proximal end 20.

Referring to FIG. 4, where is shown a stylet 22 of the present invention having an elongated hollow rigid tube 24 with a distal end 26 and a proximal end 28. The stylet 22 has a hollow flexible tubular section 30 of suitable plastic material secured over the proximal end 28 of the tube 24 for a purpose which will be described below.

Referring to FIGS. 5-7, there is shown a catheter generally designated 32 of the present invention. The catheter 32 has an elongated hollow elastic shaft 34 defining a drainage lumen 36 extending through the shaft 34. The shaft 34 has a distal end 38, and a proximal end 40. As shown, the shaft 34 has an inflation lumen 42 extending through a wall of the shaft 34.

The catheter 32 has a hollow connector 44 secured to the proximal end 40 of the shaft 34 and defining a continuation of the drainage lumen 36. The connector 44 has a side arm 46 defining a continuation of the inflation lumen 42 which communicates with a valve 48 of known type which actuates by contact of a tip of a syringe. The catheter 32 has an elastic sleeve 50 having its ends bonded to the shaft 34 in spaced circumferential zones 52 and 54 by a radiopaque material, such as by a suitable adhesive impregnated with a radiopaque material such as barium sulfate. The bonded sleeve 50 defines a cavity 56 beneath the sleeve 50 and communicating with the inflation lumen 42. The catheter 32 may be constructed from any suitable elastic material, such as silicone.

The catheter 32 has a formed or molded tip 58 bonded to the distal end 38 of the shaft 34. In a preferred form, the tip 58 is made from a radiopaque material, such as by impregnating a suitable plastic with barium sulfate. The tip 58 has an opening 60 extending through a distal portion of the tip 58 and communicating with the drainage lumen 36 for a purpose which will be described below. The tip 58 also has a plurality of drainage eyes 62 extending through the tip 58 and communicating with the drainage lumen 36 at a location intermediate the opening 60 and a proximal end of the tip 58. Also, the tip 58 defines an inner flat shoulder 64 for a purpose which will be described below.

In performing a nephrostomy procedure, first the needle 10 is passed under radiologic vision until the tip 12 is located in the renal calyces to obtain access to the kidney chamber. With the needle 10 in place, the guide wire 16 is passed through the needle 10 until the distal end 18 is located in the renal calyces, and the needle 10 is removed with the guide wire 16 in place to establish a path to the kidney K. Next, a plurality of dilators are inserted over the guide wire in order to increase the size of the path to the kidney, and the dilators are then removed.

Next, the stylet 22 is placed in the drainage lumen 36 of the catheter 32 until the distal end 26 of the stylet 22 engages the shoulder 64 of the tip 58 in order to facilitate insertion of the catheter 32. The catheter 32 and stylet 22 are then passed over the guide wire 16, with the guide wire 16 extending through the opening 60 and a lumen in the stylet 22. During this time, the stylet 22 provides rigidity for the catheter 32 to facilitate the insertion procedure. The tubular section 30 of the stylet 22 prevents kinking of the guide wire 16, and cutting of the physician's glove by the tube 24. The catheter 32 is passed over the guide wire 16 until a distal end of the catheter 32 is located in the renal calyces C. The distal portion of the catheter may be visualized on a fluoroscope due to the radiopaque tip 58 and bonding zones 52 and 54 of the sleeve 50. Next, a syringe may be utilized to actuate the valve 48, and a suitable fluid is pumped by the syringe through the actuated valve 48 and inflation lumen 42 into the cavity 56 which holds approximately three cubic centimeters of fluid in order to inflate the sleeve 50 in the renal calyces C. In a preferred form, the inflation fluid comprises a radiopaque medium 66 to assist observation of the distal portion of the catheter 32 by a fluoroscope. After inflation of the sleeve 50 in the renal calyces C, the stylet 22 is removed from the catheter 32, and a drainage tube (not shown) connected to a drainage bag (not shown) is attached to the connector 44, such that urine drains through the catheter and drainage tube into the urine bag for collection therein. In this manner, the nephrostomy procedure is performed with the catheter 32 and stylet 22 of the present invention.

According to a method of performing a nephrostomy procedure of the present invention, a guide wire is placed in a patient's body with a distal end of the guide wire located in the renal calyces, a catheter is advanced over the guide wire until a distal portion of the catheter is located in the renal calyces, and a balloon of the catheter is inflated in the renal calyces.

The foregoing detailed description is given for clearness of understanding only, and no unnecessary limitations should be understood therefrom, as modifications will be obvious to those skilled in the art.

I claim:
1. A catheter, comprising:
an elongated shaft having a drainage lumen extending therethrough, and an inflation lumen extending along the shaft;
an elastic sleeve overlying a distal portion of the shaft; and
means for bonding the sleeve to the shaft in spaced circumferential zones to define a cavity beneath the sleeve communicating with the inflation lumen, with the bonding means being radiopaque, wherein the bonding means comprises an adhesive impregnated with a radiopaque material.

* * * * *